(12) United States Patent
Holkkola

(10) Patent No.: US 7,722,502 B2
(45) Date of Patent: May 25, 2010

(54) METHOD FOR STORING EXERCISE PERFORMANCE OF USER OF EXERCISE DEVICE AND EXERCISE DEVICE

(75) Inventor: Juha Holkkola, Helsinki (FI)

(73) Assignee: Nixu Oy, Helsinki (FI)

( * ) Notice: Subject to any disclaimer, the term of this patent is extended or adjusted under 35 U.S.C. 154(b) by 912 days.

(21) Appl. No.: 11/480,864

(22) Filed: Jul. 6, 2006

(65) Prior Publication Data
US 2007/0016444 A1    Jan. 18, 2007

(30) Foreign Application Priority Data
Jul. 7, 2005   (FI) .................................. 20055395

(51) Int. Cl.
*A63B 71/00* (2006.01)
(52) U.S. Cl. .................. 482/5; 482/1; 482/8; 482/901
(58) Field of Classification Search ................ 482/1–9, 482/900–902; 434/247
See application file for complete search history.

(56) References Cited

U.S. PATENT DOCUMENTS

| | | | |
|---|---|---|---|
| 6,053,844 A | 4/2000 | Clem | |
| 6,656,091 B1 | 12/2003 | Abelbeck et al. | |
| 6,902,513 B1 * | 6/2005 | McClure | 482/8 |
| 6,949,052 B2 * | 9/2005 | Millington et al. | 482/8 |
| 7,128,693 B2 * | 10/2006 | Brown et al. | 482/8 |
| 7,212,659 B2 * | 5/2007 | Noro et al | 382/128 |
| 7,507,183 B2 * | 3/2009 | Anderson et al. | 482/1 |
| 2002/0022551 A1 | 2/2002 | Watterson et al. | |
| 2003/0013072 A1 | 1/2003 | Thomas | |
| 2004/0127336 A1 | 7/2004 | Lapcevic | |

FOREIGN PATENT DOCUMENTS

| | | |
|---|---|---|
| EP | 1 068 882 A2 | 1/2001 |
| SE | 526083 | 1/2001 |
| WO | WO 2006/060472 A1 | 6/2006 |

* cited by examiner

*Primary Examiner*—Glenn Richman
(74) *Attorney, Agent, or Firm*—Barnes & Thornburg LLP

(57) ABSTRACT

The invention relates to a method for storing an exercise performance of a user of an exercise device that is shared by several users. The invention is characterized by installing into the exercise device software for identifying the user and for collecting information on the exercise performance; assigning a first identifier to the user; assigning a second identifier to the exercise device; identifying the user in response to the first identifier; associating the first identifier with the second identifier; collecting information related to the exercise performance of the user by associating the combination of the first and second identifiers with the information related to the exercise performance; and storing information related to the exercise performance.

14 Claims, 2 Drawing Sheets

METHOD FOR STORING EXERCISE PERFORMANCE OF USER OF EXERCISE DEVICE AND EXERCISE DEVICE

This U.S. non-provisional application claims priority from Finnish Application No. 20055395, filed on Jul. 7, 2005.

FIELD OF THE INVENTION

The invention relates to shared devices providing biometric and/or mechanical information, and especially to exercise devices.

BACKGROUND OF THE INVENTION

Exercise devices and other devices providing biometric and/or mechanical information are typically used by several users in families, schools, rehabilitation centers, hospitals, the military, ships, sports institutes, and workout gyms. After a first user or fitness enthusiast has used the exercise device or other device providing biometric information, such as a treadmill, bi-cycle ergometer, recumbent, exercise bicycle, crosstrainer, rowing machine or stepper, a second user takes the first one's place to use the same device. After this, a third, fourth, or fifth user, the second user again, a sixth user, the third user again and so on may use the device.

A problem with the use of prior art devices is that the information their intelligence has stored, for instance the number of repetitions, the used resistance or preset profile, the duration of the performance, the heart rate of the user, and the energy consumption of the user, cannot be utilized after the exercise, because associating the information registered by the devices with on individual fitness enthusiast is later impossible.

BRIEF DESCRIPTION OF THE INVENTION

It is an object of the invention to develop a method and an apparatus implementing the method in such a manner that the above problems can be solved. The object of the invention is achieved by a method and system characterized by what is stated in the independent claims. Preferred embodiments of the invention are disclosed in the dependent claims.

The invention is based on the fact that client software installed in the exercise device or other device collecting biometric and/or mechanical information is able to dynamically, automatically authenticate each individual user by utilizing wireless authentication technologies, to store the biometric and/or mechanical information provided by the device, to associate in the manner described above the identity of the authenticated user with the information produced by the same user on the device, and to transmit by using either a fixed or wireless TCP/IP local area network the identity-information pair collected in the earlier described manner to a centralized database installed in a (remote) server, in which the collected information can be analyzed and managed centrally. In addition, the server may run a separate web server, whereby users may be provided remote read rights to the information managed in the server.

It is an advantage of the method and system of the invention that it enables the dynamic identification, authentication of individual users and that information stored by shared exercise devices or other devices providing biometric and/or mechanical information can be associated with an individual user later, which makes it possible to utilize the provided information after the actual use of the device.

BRIEF DESCRIPTION OF THE FIGURES

The invention will now be described in more detail by means of preferred embodiments and with reference to the attached drawings, in which.

DETAILED DESCRIPTION OF THE INVENTION

Figure 1:
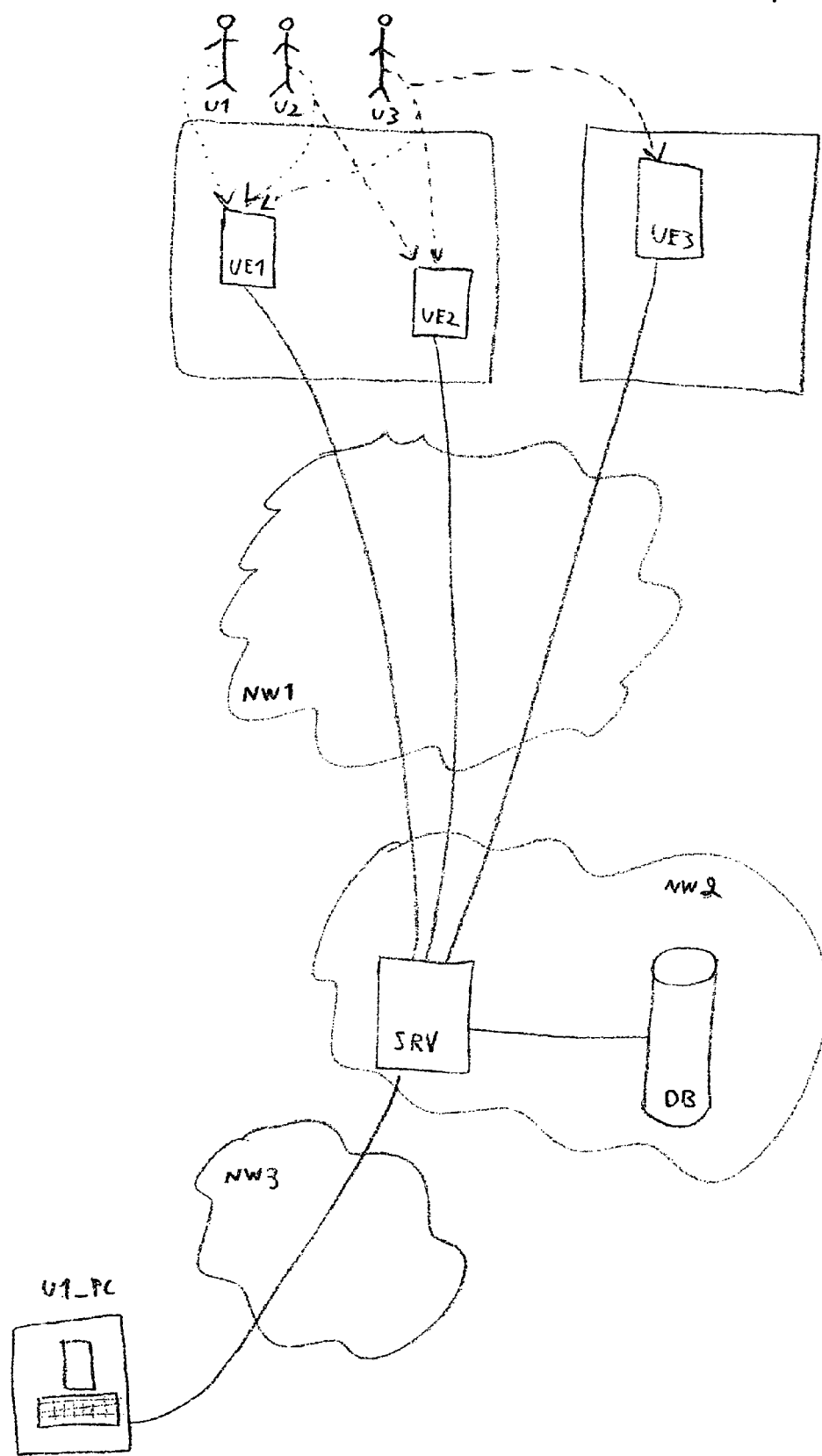
FIG. 1 shows a system of shared exercise devices according to the invention and one of its preferred embodiments.

FIG. 1 shows a system according to the invention and one its preferred embodiments, in which different users or one and the same user uses the exercise device. The exercise device may be a shared device, which means that several users may use the same device either one after the other or at the same time. The device may also be used by only one user.

In the case of FIG. 1, users U1, U2, and U3 use exercise device UE1 in turns, and users U2 and U3 use exercise device UE2 in turns. In addition to this, user U3 may also use exercise device UE3, which is in a different space than exercise devices UE1 and UE2. Over communications network NW1, user information may be transferred to and/or stored on server SRV in another network NW2 and in database DB connected to server SRV. It is also possible to connect several servers and databases to the system.

U1_PC depicts a user device, such as a home computer, portable computer, communicator, or wrist-held monitor/analyzer, with which user U1 can during the exercise or after it check his or her own performance by accessing the stored information on the above-mentioned server SRV, for instance, over network NW3. The server may also have various application programs and analysis applications for further processing the information.

According to another preferred embodiment, several different users U1, U2, and U3 may simultaneously use an exercise or sports device UE1, UE2 and receive information on their performance immediately or later for perusal. It is then possible to give the same information as the performance information for each user, if the device only registers one set of performance information. Alternatively, each user can be given his or her own performance information, if the device is capable of registering personal performance information for each user. This may be done in such a manner, for instance, that the device is divided into two or more parts and each part will receive a specific identifier. This identifier can then be associated with the identifier of the user of the part. The device can also be divided into parts in such a manner that a first group of parts receives one and the same identifier and the parts in a second group receive each their own identifier.

Figure 2:
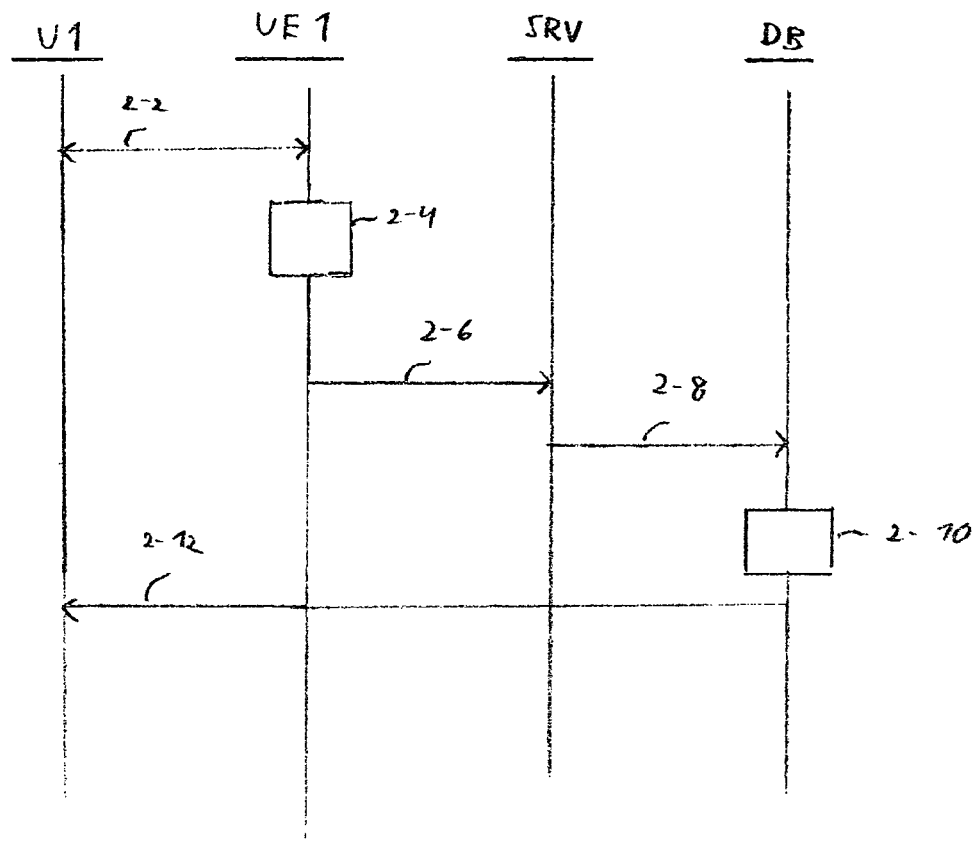
FIG. 2 shows a signaling diagram of the invention and one of its preferred embodiments for storing a performance.

FIG. 2 shows a signaling diagram of the invention and one of its preferred embodiments for storing a performance. After software for identifying a user of the exercise device and for collecting information on the performance of the user is installed in the exercise device, the user may in step 2-2 enter his or her own information to exercise device UE1. A temporary or a permanent identifier of the user can be used in this.

The information can be entered using a display in the exercise device. Alternatively, or in addition to the above, it is also possible to use a wireless authentication technology, for instance RFID (radio frequency identification) or Bluetooth technology, to identify the user.

When using RFID technology, the fitness enthusiast may have an RFID sticker attached to his or her wrist, clothes, shoes, heart rate monitor and/or sports equipment so as to identify the user and to record the data on the sticker on the server. The used device then has an RFID reader that identifies the user and transmits the information on to the server.

When using Bluetooth identification, the user can be identified by a Bluetooth signal transmitted by user equipment, such as the user's mobile phone.

As described earlier, it is also possible to create for the exercise device one or more identifiers that distinguish the exercise device from other exercise devices and/or distinguish between the various parts of the exercise device.

The exercise device may then check the information provided by the user and, after approving the information, provide them to the user for confirmation. Thus, the user of the exercise device can for instance be identified in response to a first identifier provided by the user, and the first identifier of the user can be associated with the second identifier of the exercise device. This way, each user can have his or her dynamic identifier pair, i.e. user-specific information. This user-device identifier pair can be transmitted on in one burst to a server.

In the authentication of the invention and one of its preferred embodiments, it is possible to use double authentication, in which the client-server architecture's a) server identifies the client by using a static identifying code, and b) client identifies the user of the exercise device dynamically by using a wireless authentication mechanism, such as RFID or Bluetooth.

Using dynamic authentication, a client installed in an exercise device can associate the identity of the person working out with the data provided by the device and transmit them on to the server for storage and analysis, for instance. Without dynamic authentication, transmitting data to the server would be useless, since all the data stored therein would be one big mass of data whose further processing would be rather futile.

After the user information is read and approved, the user is authenticated to the user equipment, which may comprise, for instance, that the user has the right to use an exercise device and/or the user may receive information on his or her individual performance. It should be noted that the user could be identified prior to the exercise, during it, or after it.

The identification, authentication of a user is a requirement for storing information provided by intelligent exercise devices for possible further processing. Intelligence means for instance that the (exercise) device can measure and store information on exercises made with it; examples of this are a treadmill recording running time, energy consumption, distance, mean speed, etc.; and an exercise bicycle recording heart rate, resistance, pedaled distance, mean speed, top speed, energy consumption.

As described above, several different communications methods and networks can be used to remotely identify and automatically authenticate the user of a device. The user of the exercise device is then identified automatically and/or wirelessly with the client program installed in the exercise device.

In step 2-4, the exercise device collects information related to the exercise performance of the user. Information can for instance be collected with a client program installed in the exercise device, which can store information defined during installation, related to the exercise, and provided by the intelligence of the exercise device. The information can for example be information related to the performance and stored by the exercise device and/or mechanical information of the device, such as the number of repetitions, used resistance, preset profile, traveled distance, lifted mass and/or the duration of the performance. The information can also be biometric data related to the user and/or environmental information, such as the heart rate, blood pressure and/or temperature of the user and/or the temperature, air pressure and/or moisture percentage of the environment.

It is also important that the information can be associated with the identity of the user, whereby the intelligence of the exercise devices used in accordance with the invention and its preferred embodiments can be utilized user-specifically. This may be done with the client program, for instance, in the manner described above, in which the user is identified before the exercise begins, and the information that is transmitted for storage is associated with the user until the user stops using the exercise device. Alternatively, a group of users can preliminarily be identified before they start their exercise, and during the exercise, each user can be distinguished by a given temporary identifier, such as a number, mark and/or code, or permanent identifier, such as a number, mark, code, fingerprint and/or sound.

The client program installed in the exercise device can transmit the extracted information, information related to the exercise performance of the user and user's identity to the server for centralized data management by using several different communications methods and networks, for instance a fixed or wireless TCP/IP connection. The fixed connection may be a LAN (Local Area Network) connection, and the wireless connection can be a WLAN (Wireless Local Area Network), GPRS (General Packet Radio Service) or UMTS (Universal Mobile Telecommunications System) connection. In step 2-6, the information is then transmitted to the server and in step 2-8 to the centralized database. In step 2-10, the information can be stored in a database DB. The server can receive information transmitted by one or more clients and store it. Storing enables centralized management of the stored information, its association with certain user identities, analysis and storage for later use. Information can also be stored in the exercise device, in its cache memory, for instance.

The information can also be temporarily or permanently stored on the user device or server. In addition, information can be transmitted to one or more users either in real time or in delayed mode directly from the user device or database in step 2-12.

According to a preferred embodiment, a client of a client-server architecture installed in an exercise device may register and detect, sense intelligent electric information provided by the device and transmit it with a transmitter to a server, and the server may receive information transmitted by the client. Both the server and the client may be set or defined an identifying code, on the basis of which the server may identify the client transmitting the information. For instance, in a workout gym environment this makes it possible for the server to identify which exercise device client is transmitting the information received by the server.

In such a case, it should, however, be ensured that the information transmitted by the exercise device or client connected thereto can be associated with the exercise done by an individual person and that the identifying code transmitted by the client and identified by the server provides this information. Workout gym devices shared typically by several users can then also be used to obtain personal information from one user.

Figure 3:
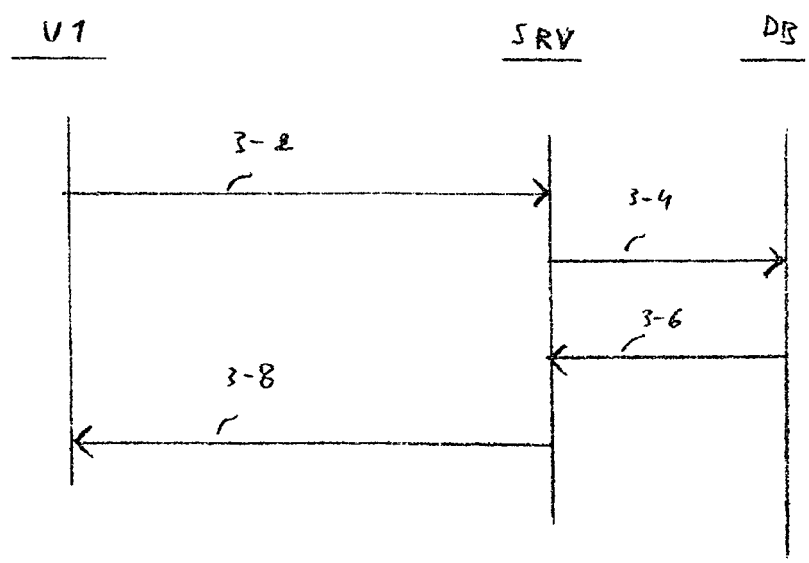
FIG. 3 shows a signaling diagram of the invention and one of its preferred embodiments for checking a performance.

FIG. 3 shows a signaling diagram of the invention and one of its preferred embodiments for checking a performance. In step 3-2, user U1 may establish a connection to the centralized server for a further analysis, remote reading and/or storage of his or her own and/or other users' performances. In step 3-4, server SRV searches for information from database DB, and the database returns the information to the server in step 3-6. After this, the information can be returned to user U1 in step 3-8.

The user can thus be granted remote read rights to information related to an exercise performance through one or more data networks, which may be mobile networks and/or networks according to the Internet protocol, for instance. According to a preferred embodiment, the server runs a separate Internet web server with which the users can be granted a TCP/IP-based remote read possibility to the information in the server.

According to another preferred embodiment of the invention, several persons using the same device or monitor, such as a heart rate monitor, can receive their own individual information concerning their exercise and/or heart rate and/or energy consumption during the exercise or after it. This way people living in the same household and/or using the same heart rate monitor can check whose information are in the heart rate monitor at each time. This is possible, because the sensor-transmitter pair can identify the current user dynamically by using RFID technology, for instance. Both biometric information and the associated level two dynamic identity (item b above) can for instance be transmitted to the heart rate monitor, whereby it shows both the biometric information of a performance and the identity of the person who did it.

Other preferred devices according to the embodiment are, for instance, thermometers, blood pressure gauges, blood oxygen content gauges, and alcometers, i.e. gauges and devices that can be shared by several different users.

The invention and its preferred embodiments can be used in many different sports devices, such as exercise devices, including treadmills, bicycle ergometers, recumbents, exercise bicycles, crosstrainers, rowing machines and steppers, various tackles, abdominal muscle machines, dorsal muscle machines and peck-decks.

Gym equipment may be located in one or more spaces that may even be far away from each other. Information collected by the equipment can be stored in a database DB in a workout device or separate from it.

The invention and its preferred embodiments may be applied to situations, in which one and the same user uses the device or devices or in which it or they are shared and used by several different users. In addition, it is possible to provide the users with one or more identities.

The invention and its preferred embodiments provide the advantage that mechanical information stored by the exercise device intelligence, for example the number of repetitions, used resistance or preset profile, and duration of the performance, can be utilized after the exercise, because the information registered by the devices can later be associated with the person doing the workout. Each user can then receive information on his or her own exercise, even though several users share the devices.

It is apparent to a person skilled in the art that as technology advances, the basic idea of the invention may be implemented in many different ways. The invention and its embodiments are thus not restricted to the examples described above, but may vary within the scope of the claims.

The invention claimed is:

1. A method for storing an exercise performance of a user of an exercise device that is shared by several users, comprising:
   installing, into the exercise device, software configured to identify the user and to collect information on the exercise performance of the user;
   assigning a first identifier to the user of the exercise device;
   automatically identifying the user of the exercise device in response to identification of the first identifier by the software in the exercise device;
   associating the first identifier with a second identifier that is associated with the exercise device;
   collecting information related to the exercise performance of the user in an automated manner from the exercise device without input by the user by associating the combination of the first and second identifiers with the collected information related to the exercise performance of the user on the exercise device; and
   storing information related to the user's exercise performance on the exercise device in memory accessible by the software installed in the exercise device.

2. The method of claim 1, comprising identifying the user with a fixed authentication technology or one of the following wireless authentication technologies: RFID, Bluetooth.

3. The method of claim 1, comprising transmitting information related to the exercise performance of the user to a centralized database installed on a server and storing information related to the exercise performance into said database.

4. The method of claim 3, comprising transmitting information related to the exercise performance of the user to the centralized database installed on the server by using a fixed and/or wireless TCP/IP connection.

5. The method of claim 1, comprising associating the first and second identifiers and/or a combination of the identifiers and the information on the exercise performance in the exercise device and/or server and/or database.

6. The method of claim 3, comprising granting the user rights to the information in the database in response to the identification of the user.

7. The method of claim 5, comprising granting the user rights to his or her information only.

8. The method of claim 1, wherein the exercise device comprises two or more parts and that at least two parts are assigned different identifiers.

9. The method of claim 1, comprising storing information related to an exercise performance of one or more users using the exercise device simultaneously.

10. The method of claim 8, wherein regardless of the first identifier of the user, two or more users are given the same information.

11. The method of claim 3, wherein the database is in the exercise device.

12. The method of claim 1, comprising providing the user with remote read rights to the information related to the exercise performance over a data network.

13. The method of claim 12, wherein the data network is a mobile network and/or an Internet protocol network.

14. The method of claim 4, wherein the database is in the exercise device.

* * * * *